United States Patent [19]
Devlin

[11] Patent Number: 5,998,697
[45] Date of Patent: Dec. 7, 1999

[54] TRANSGENIC FISH AND VECTORS THEREFOR

[75] Inventor: Robert H. Devlin, North Vancouver, Canada

[73] Assignee: Her Majesty the Queen in right of Canada, as respresented by the Minister of The Department of Fisheries and Oceans, Ottawa, Canada

[21] Appl. No.: 08/331,081

[22] Filed: Oct. 20, 1994

[30] Foreign Application Priority Data

Jun. 17, 1994 [CA] Canada ................................. 2126138

[51] Int. Cl.⁶ .............................. C12N 5/00; C12N 15/00; C07H 21/04
[52] U.S. Cl. .............................. 800/20; 800/21; 435/325; 536/23.51; 536/24.1
[58] Field of Search .............................. 800/2; 435/172.3, 435/320.1, 240.2, 6, 69.1, 70.3, 375, 377; 935/6, 9, 10, 13, 23, 24, 34, 53, 70; 536/23.51, 24.1

[56] References Cited

U.S. PATENT DOCUMENTS 5,545,808  8/1996  Hew et al. ................................. 800/2

FOREIGN PATENT DOCUMENTS

WO 92/16618  10/1992  WIPO ............................ C12N 15/00

OTHER PUBLICATIONS

J. Watson et al., The Molecular Biology of the Gene, Benjamin Cummings Publ. Co., Menlo Park CA ('87), pp. 716–717.
R. Guyomand et al., Biochimie 71:857–63 ('89).
T. Chen et al, Transgenic Models in Med. & Agric. Wiley–Liss, Inc. ('90), pp. 127–139.
Z. Liu et al. Bio/Technology 8:1268–72 ('90).
M. Zaffarvllah et al. Mol. Cell. Biol. 8(10):4469–76, ('88).
W. Connec et al. J. Mol. Evol. 20:236–50 ('84).
B. Johansen et al. Gene 77:317–24 ('89).
L. Gonzalez—Villasenoc et al., Gene 65:239–246 ('88).
I. Guthrie et al. N. Am. J. Fish Man AG. (188) 8(4):442–54.
J–K. Lu et al. Mol. Marine Biol. & Biotech. (192) 1(4/5):366–75.
Seq. Search result—comparing SEQID #2 to Genbank Acc #M22487.
Seq. Search result—comparing SEQID #1 to Genbank Acc #X01064.
B. Cavari et al., Fish Physiology and Biochemistry, vol. 11, No. 1–6 pp. 345–352 (1993).
S.J. Du et al., Bio/Technology, vol. 10, pp. 176–181 (1992).

*Primary Examiner*—Bruce R. Campell
*Attorney, Agent, or Firm*—McFadden, Fincham

[57] ABSTRACT

Sockeye salmon growth hormone genes Types 1 and 2, and sockeye histone and metallothionein gene promoters have been isolated and sequenced. Terminator sequences for the growth hormone gene have been found. Vectors containing these promoter and terminator sequences (and intermediate sequences) have been prepared and used to transform fish egg cells. Transformed fish egg cells have been grown into transgenic fish. In the case of inserted full-length growth hormone gene, both accelerated growth and early smoltification were observed. An aspect found beneficial is to combine homologous fish metallothionein or histone gene promoter with fish gene, preferably growth hormone gene, terminator in the same vector, for preparing transgenic fish.

8 Claims, 1 Drawing Sheet

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 509 base pairs
      (B) TYPE: nucleic acid
      (C) STRANDEDNESS: single
      (D) TOPOLOGY: linear (xi) SEQUENCE DESCRIPTION: SEQ ID NO:1:

```
GAGAAGGCCG TCAAAGCCAA GTAAAATCGC TGGTGCGGCT GCAACTTGAC TACTCAACCC      60

CCAAAGGCTC TTTTAAGAGC CAACCACCTG GCTCAGCCAA AAAAGCAGTG TCCTCTCTCT     120

CTATGGCTGG CCAACTATTT GGCGTGTTTG TTAAATACAC ACACATATAC ACGGCACAGT     180

ATCAAGTGCC CACATGAGGC CTACATGAAG AATAACAACT ACTAGGCTAA AATGAAGAGA     240

AGCGTTATTG CCCGTAAAGT GTAACGTTGC TCGCGGCCCT AACAAAAGAA CCAAGCAGCG     300

CCTCGGCGAG GGATGGGGGT TGCATTTTGG GGCGTCACGG AGAGGTCCGA GCCTCCCGTC     360

CAATGGGCGG AGGAGGCCTC CGCAACGGGC CAATCAGGGC GGTGCGGAGA TGGTGACCAA     420

TCAGCAGACG CCGCTGCCGG CTTTATAAAC TTCACATAGG CATTTGGAGG CTATACTCCG     480

ACTGTGAAAG AAGGAAGCTA CGTAGCGCC                                      509
```

(2) INFORMATION FOR SEQ ID NO:2:

(i) SEQUENCE CHARACTERISTICS:
      (A) LENGTH: 318 base pairs
      (B) TYPE: nucleic acid
      (C) STRANDEDNESS: single
      (D) TOPOLOGY: linear (xi) SEQUENCE DESCRIPTION: SEQ ID NO:2:

```
CTGATTAAGT TTTGTATAGT TAAATAAATA TAGGTGTAGC CTTAATTAAT CGATGATCAA      60

CGTGGTAATC AGGTTTATGT AACAGGCTAT GGAATTTGGA AACAATAGGA AACTCTTCCT     120

TGATTATTTT CGCGCAGTAT AATGAAATAA CCCGGGTGCA AACCCTGATC GTCTGAACGC     180

GAGACTGTTT TGCACACGGC ACCCGTCTGT CCCTGACGCT ATAAAAACGG TCTTCGCCAA     240
```

| | |
|---|---|
| AGAGAAATTT AAAGCTTACA ACTCAACAGT GAAATTGAGC TGAAATACTT CATTTGACTA | 300 |
| AAGAAGCGCG ATCGAAAA | 318 |

(2) INFORMATION FOR SEQ ID NO:3:

(i) SEQUENCE CHARACTERISTICS:
        (A) LENGTH: 4744 base pairs
        (B) TYPE: nucleic acid
        (C) STRANDEDNESS: single
        (D) TOPOLOGY: linear (xi) SEQUENCE DESCRIPTION: SEQ ID NO:3:

| | |
|---|---|
| GTGTGCGCGT GCGTGCGTGT GTGTGTGTGT GTGTAACTTG TGTCCATTCA | 50 |
| TTACATCCTA GACAACAGAG GTTTGTGTTG TATGTGTTTT GACCCTAATT | 100 |
| CGTTCAGTCA TCAAGTAAGT AGTTTTTTTA GGACACCTCC CCTCTTCCCA | 150 |
| AACTCATGGA AAAATGTATG ATTGATTTGA CGTAATATGG TAATTGTTCC | 200 |
| ACAATCACAT ACAGAAACAG GTCCTATCAA TGAAAGGTGG TAAAGGGATG | 250 |
| AAAATCTCAT GGGTCCTCCT ATTGATACAT TAAAACATGG ATTCCCCGTC | 300 |
| TATAAAAACA GTGGCCCCAA ACAAACGACA ACATACTCAA CCGACCACCG | 350 |
| CACTTTCAAG TTAAGTAACC ATCCTTGGCA ATTAAGAGTA AAAATGGGAC | 400 |
| AAGGTAAGCC TGCTTTTTCT GTATATTTCT TTTTTCAGTG GGAAGTCAGT | 450 |
| GTACCATTTA GTACAATTTA ACTAACTGCT ATGAGGTTAT AATCTATTGA | 500 |
| CACAGAACAA CCTGCTTTAA CAACCTAACT ATGTGATCAA TAACATTTAC | 550 |
| ATTTGAGTCA TTTAGCAGAC ACTCTTATCC AGAGCGACTT ACATGAGCAA | 600 |
| TTGGGGTTAC GTGCCTTGCT CAAGGGCACA TCAGATTTCT CACCTAGTCA | 650 |
| GCTCTGGGGT TGAAACCAGT AACGACCCAG CGCTCTTAAC CCGCTAGGCT | 700 |
| ATTGGTGTAT GATGGCTGAG AAAATCTTAC TAATGTATCT CACCATAATT | 750 |
| CGACTTACTC GTTTTCTACA TTTCTTATTT GAATCTCTCT TTTAGTGTTT | 800 |
| CTGCTGATGC CAGTCTTACT GGCCAGTTGT TTCCTGAGTC AAGGGGCAGC | 850 |
| GATAGAAAAC CAACGGCTCT TCAACATCGC GGTCAGTCGG GTGCAACATC | 900 |
| TCCACCTATT GGCTCAGAAA ATGTTCAATG ACTTTGTAAG ACAGCTTTTG | 950 |
| AATCTTCTTT GGACATATCA AATAGTGTAT CAATGATTGT TCTTCTTCTT | 1000 |
| GTAGACAGTG TCCTCTTCAC ACAACCCTCG TGGCTAAAAA AATCTCTCTC | 1050 |
| TCCCTTTGTG ATTTTGTGCA GGACGGTACC CTGTTGCCTG ATGAACGCAG | 1100 |
| ACAGCTGAAC AAGATATTCC TGCTGGACTT CTGTATCTCT GACTCCATCG | 1150 |
| TGAGCCCAGT CGACAAGCAC GAGACTCAGA AGAGTTCAGT AAGTAACCTG | 1200 |
| GCTGAGACAA TTACGCATGT TATGCCCTGT AAAGTGTCAA ATCGTGACAG | 1250 |
| TTCCACTCTG CTATTCACCT TAAATATGAA CTCCTCCATG ATGCAAGATT | 1300 |
| CCAAAAATAA ATAATAGGGC ATCTCAATTT GAACAATCGA TAGAACTTAG | 1350 |
| TCATTAGTTA TTGGGCAAGC AGACCACCAA TTATGTCAAC TCAAATTTAT | 1400 |
| AATTTTTTAT TTAAATTTTA TTTGAACCTT TAATTAACTT GGCAAGTCAG | 1450 |
| TTAAGAACAA ATTCTCATTT ACAATGACAA GCAGAGGCAG CATCATGCAT | 1500 |
| GGCTCTCGAG TGGCACAGCA GTCTAAGGCA CTACATCTCA GTGCCAGAGG | 1550 |
| CATCACTGCA AACCCTGGTT TGATTCCAGA CTGTATTTCA AGCGGCTGTG | 1600 |

| | |
|---|---|
| ATTGTGAGTC CCATAGGGCG GCACACAATT CTCCCAGCGT CGTTAGGGTT | 1650 |
| AGGGTTGCAA TACCTCAGTG TTTTTCAACT AAGGTAGATA AAACAACCAC | 1700 |
| ATATCATTGC AAGTAAAACC ATCACTGTCT AATCGGTGGT TTCTCTACGT | 1750 |
| CTACATTCTC TGTTTTGTGC TTTTCTGTAC AGGAAACCCG CCCCAAAAGT | 1800 |
| ATTTCACTCA ATCATGTAAA TAGGGCATCT CAAGCTGTAC AATACAACTC | 1850 |
| AACTTAATTT TCCAATAATC TGTGGTTTCT CTACATCTTC ACACACAGGT | 1900 |
| CCTGAAGCTG CTCCATATTT CTTTCCGTCT GATTGAATCC TGGGAGTACC | 1950 |
| CTAGCCAGAC CCTGATCATC TCCAACAGCC TAATGGTCAG AAACGCCAAC | 2000 |
| CAGATCTCTG AGAAGCTCAG CGACCTCAAA GTGGGCATCA ACCTGCTCAT | 2050 |
| CACGGTAAAG AAAGGAGGGA GAACAATGAC CATTTGTGGT GTCACACTTT | 2100 |
| GTGCACTGTA AACTCCAAGG CATTTTTAAC TCAAATACTT CTAGTGAGTT | 2150 |
| GAACTCAAAG TCAATGAAAA ATCCTTATTG CTTAAAATGT TTATGTGGTA | 2200 |
| CTGGCTCAAA ACTAAATGAG AAGTCACATC AATGCAATTT TTTAAAGTTA | 2250 |
| TAACAAATTC ACTTTTACCA AGCATGCTCT ACTGCAGGTA GAATTTTTAA | 2300 |
| AAAAAAAGTT TTTAACGATC TGTGTTTTTG CATGTACAGA ACATTGAGTG | 2350 |
| ATTGATTCAT TTTATGCTAC ACAAAGAAAC ATAACATACG TTTCAACGTT | 2400 |
| TTCACAAAGA TTAACAAGTC ACCAGAATTC TGCAAACTCA ACTTGCAGGC | 2450 |
| CTGATGTGGC CTGTATACCA TGAGTTTCAG GCCACTGTAT TAGGGTAAAG | 2500 |
| CTACGCCTCA AAATAAGGTC TTATGAGATA AGTAATGTAT TGTTGTAAAG | 2550 |
| AGCTGAATTA TCATGATAAT ATTTGCCTAG GAATTCACTT GAAGGCCACA | 2600 |
| GGACTGAAAA TGAATGACAA CAGCCATGTC TCTGTCACTA ACATATACAG | 2650 |
| TCATGGGTGA TAACTACACT TCACTCAAAA AGGCCAGGCA CACTGGGAAA | 2700 |
| TTATATTTGA GACGTGGCTT AGTGGGGGCA TTACTAAAAA ATGTCAAGCT | 2750 |
| GATACAACTC AAATCTGGAC ACATCACAGG GTGACTCTAT AGGTTTGAGT | 2800 |
| AATGACTGAC TATAACATCA CTTTAAGTAA CTGCAGTCAG ATTCTGTATA | 2850 |
| TTAAGTGCAA CGGGTTTCCT AAAAAAGTGT TGAGTAATGG CAGCACATTG | 2900 |
| GGGTTTGCAG TGACATGAAA GGGAAATATC TGTATGCTTT CCTAGTTAGA | 2950 |
| AAGCATAGTG TAGGACCACG TATGCCTCTT CTCAGCAGAT CTTTCAGGGC | 3000 |
| TTTACATTGT GATGTGGTAA CTGACCTTAT CTATCATCGT GATTGTATCA | 3050 |
| GTGACACCCC ATTCAATGAC TGAATATCGC CCCATTCAAG GACATTTATG | 3100 |
| CATGTGTCTT TTGCTACGTG TGCTTTCAGA AAGGCCCAAT AAGCAAATAT | 3150 |
| TGATATGCAC ACATCCACCC CACCATGCAT CTCTCTCTGT CTCCCACAGG | 3200 |
| GGAGCCAGGA TGGCGTACTG AGCCTGGATG ACAATGACTC TCAGCACCTG | 3250 |
| CCCCCCTACG GGAACTACTA CCAGAACCTG GGGGGCGAAG GAAACGTCAG | 3300 |
| GAGGAACTAC GAGTTGTTGG CTTGCTTCAA GAAGGACATG CACAAGGTGC | 3350 |
| GCAACCATGT TGCCTTCAAT TTCATGTGCC TTCCTGTATT TTCTACAGTG | 3400 |
| CATTGTTTTT TTGTGTTCTC TATTGCAAAG TATTGTTAGT AAATAACTCA | 3450 |
| CGGACACTAG AGAAGCTTTA ACCAAGTTTA ATTCTTCCCA AAGGTTCTGT | 3500 |
| ACAGCTGTAA TCGACAGCA AAACATTTCA CTCCACAGTC ATATACATCC | 3550 |
| TACTTAAAAC ACTCCTTCTT CAATCCTTAT AGTTTATGGC TCCACAGGAA | 3600 |

```
GCTAATAAAG AGGGTAACAG GACAACAAAC CTTTATTACT GCCTTCAGAG        3650

AATCTGTCCT CACCTCCTGA CCTCAACCCC TCATCTAATC CACAGATGTC        3700

CATTGTTTTT TTCAGAGAAC CATTAAGTTC TGACATAACC CAGTTTCTTT        3750

CATTTACTAT CTCAATGATC AACGTTTAGC CAATTCCAAC AGTATCTTTG        3800

GGACTTTAAC CCATATATTA CTATTATTGT TCATTGATCA AGACTGTTCT        3850

CGAGAAAGGT CTGGTGACCT AGAACACACA CATTAAAATG TGTCAACTAT        3900

AACCCATTCT TTTTCTTTTT TCCCCCCCCG AGGTCGAGAC CTACCTGACC        3950

GTCGCCAAGT GCAGGAAGTC ACTGGAGGCC AACTGCACTC TGTAGACGTG        4000

GGCTGGAGAG GCAGCCAGCA AGAGCCTGTC TCCAGGGTTC GGTTTCCCAT        4050

ATACAGATTA GGCCTTGCCC TGCACTGAGG TGCATTTTCA ATTGAGATTC        4100

TCCATTAAAC ATGCTTTTCA GTCTAGAGTA ATTTTATTTT GTATCTGGTA        4150

GAGCCTGACT CCAGGAGTTT TCAGGCATTT GCATTTTTTT CTCTGAAATC        4200

AACAACAACA CTTTCTATAT TGACTCTATC ACTCTGAGCT ACCATTGATT        4250

AGTACATTTA TAGAAAAGGT TATTACATGT GCTACTGTTT ATGCATATGT        4300

TAATATTTAG GGGTGAAATG GGAACTTGTA GAGCTCCAAG CTTTTGGATA        4350

ATATATTTTA GAGTAATTTC CTTTTAGTAT TTTCATTCCT TAATCTTATT        4400

GTTTGAAACT AATAGTGATT CATGTTTCAA TAAAGATGTT CTTCTCTGCA        4450

GCACATGATC TCTTGGCTTC TATTTAATAT CTTTCAAATC AACATTTTTT        4500

ACAAGTTCCT AGCCCCAACA TTCCTATGAT GTCTCTCGGA CAATTTAGGG        4550

CCTGGATTCA ATCCGTATCG CAGACGCTCC ATTGAAATGT AAAGGCAATG        4600

TTCCTGCGTT CGCGGAGACT GCATTCACTT CAAACGCTGC TGCATATGTC        4650

GGCTCAATCG GAAATAACCT GAAAAATGTT ACACGGTTCT TCAGCGATAC        4700

GGATTGAATC CAGCCCATAG TTACGTACAT TTGTATTGGC AAAA           4744

(2) INFORMATION FOR SEQ ID NO:4:

(i) SEQUENCE CHARACTERISTICS:
        (A) LENGTH: 3872 base pairs
        (B) TYPE: nucleic acid
        (C) STRANDEDNESS: single
        (D) TOPOLOGY: linear (xi) SEQUENCE DESCRIPTION: SEQ ID NO:4:

TTTGTTCATT CATTATGTCC TAGACAACAG AGGTTTGTGT CGTATGTGTT           50

TTGCCCCTCA TTTGTCAAGT CATCGAGTAC GTTGTTGTTT TAGGAGTCA           100

CCTCTTCCCG AACTCATGGA AAAATTCATG ATTGATTTGA CGCATTATAC          150

TGATTCTTCC ATAGTCACAT ACAAAAACAG GTCCCATCGG CGAGAGGTGG          200

TACATGGAGA AAATCTCATG TGTCCTCCTG TTGATACATT AAAACATGTA          250

TTCCCCATCT ATAAAAACAG TGGCCCCAAA CAAGCGGCAA CATACTGAAC          300

CGACCACCAC ACTTTCAAGT GAAGTAAATC ATCCTTGGCA ATTAAGAGAG          350

AAAATGGGAC AAGGTAAACC AGCTGTTATT TTATTTTTTA AGTGGGAAGT          400

CAGTGTACCA TTTAATACCA TTTAACTTGA ACATTTAATC ACTGAGGCAG          450

GAGCCAACAA GGCAGAGAAA GAGTGAACTA ATAATTACTA ATAGTAATGT          500

ACTGCCATGA GGGTATAATC TACTTACACA GAACCACTTC CTTTAATTAA          550
```

-continued

| | |
|---|---|
| CAACGTGATC TATTAGGTTT ACATTTGAGT TAGTTAGCAG ACGCTCTTAT | 600 |
| CCAGAGCGAC TTACAGCAAT TAGGGTTAAG TGCCTTGCTC AAGGGCACAT | 650 |
| CAACAGATTT CTCACCTAGT CAGCTCAGGG ATTCAAACCA GTAACCTTTC | 700 |
| AGTTACTGGC TCAACGCTCT TAATCACTAG GCTATTGATG TACAAAGGCT | 750 |
| GAGAATGTCT TACTAACATG TCGCAACATA ATTTGACTTA CTCGTTTTTA | 800 |
| TACATTTCTT ATTTTCTTTC ATCTCTCTTT TAGTGTTTCT GCTGATGCCA | 850 |
| GTCTTACTGG TCAGTTGTTT CCTGAGTCAA GGGGCGGCGA TGGAAAACCA | 900 |
| ACGGCTCTTC AACATCGCAG TCAACCGGGT GCAACACCTC CACCTATTGG | 950 |
| CTCAGAAAAT GTTCAACGAC TTTGTAAGAC AGCTTTTGAA TCTTCTTTTG | 1000 |
| ACACAGCAGA TAATGTTTCA GAGGTGGTTC CTCTTCTTTG TAGACAAGTG | 1050 |
| TCCTCTTCAC GCAAACCGAG CGGCAAAACA TTCTCTCTCC CGTCTTTGTG | 1100 |
| ATTTTGTGCA GGAAGGCACC CTGTTGTCTG ATGAACGCAG ACAGCTGAAC | 1150 |
| AAGATATTCC TGCTGGACTT CTGTAACTCT GACTCCATCG TGAGCCCCAT | 1200 |
| CGACAAGCAG GAGACTCAGA AGAGTTCAGT AAGTTACCGG GCTGAGACAA | 1250 |
| TCCTCCATGA TGCACAATTC CAACATGAAT AATAGGGCAT CTCAAGTTGA | 1300 |
| ACAATCGATA CAACTTAGTC ATTAGTTATT GGGCAAGCAG ATCCCCGATT | 1350 |
| GTCTAAACTC CATGGGTAAA TATATACTGT AGATAAGAAG AACCAGCATC | 1400 |
| ATGCATGGTA GAAATTAAAT CTAGCCATGA CAGGGAGTTT TAAATTGTAC | 1450 |
| ACTTAAAATC GGCAGGAAAA TGTTGCTATA CCTCAGTGCC TTCAAAAACA | 1500 |
| ACCACATGTC ATAGTCCTTG TAAGTAAAAC CCATCACTCT CTAATCGGCG | 1550 |
| GTTTCTCTAC GTCTACATTC TCCAGCAATG TGTCATGTAA ATGATATGGC | 1600 |
| ATCTCAAGCT GTACAATTAC AACTCAACTT CATTTTCTAA TAATCTGTGG | 1650 |
| TTTCTCTACA TCTACACACA CAGGTCCTGA AGCTGCTCCG TATCTCTTTC | 1700 |
| CGCCTGATTG AATCCTGGGA GTACCCTAGC CAGACCCTGA CCATCTCCAA | 1750 |
| CAGCCTAATG GTCAGAAACT CCAACCAGAT CTCTGAGAAG CTCAGCGACC | 1800 |
| TCAAAGTGGG CATCAACCTG CTCATCGAGG TAATGGTCAA TTACCATTTG | 1850 |
| TGGTGCCGCA CTTTGTGCAT TTTTAACTCA AATACTTCTA GTAAGTTGAA | 1900 |
| GTCAGTCAAT GAAAAGTCAT TATTACTTCA AATGTCTATG TGGTACTGGC | 1950 |
| TCAAATCTAA ATGAGTCACA TCAATGCAAT TTTTTAAAGT TATAACAAAT | 2000 |
| TAACTTTTTA CCCAGCACGC TCTACTACAG GTAGATTTTT TGGAATTGTT | 2050 |
| TTTAATATCT GTGTTTTTGC ATGTACAGTA CATTGAGTGA TTGATTCATT | 2100 |
| CATTCATCTT ATGCTACACA CAGATATATA ACGTACATTT TTCTACATTT | 2150 |
| TCACAAAGAT AAATAACATA CAAGGTACTG GAATTTTGCA AACCTACTTG | 2200 |
| CAGGCCTGAT GTGGCCTGTA AACCATGAGT TTCAGGCCAC TGTATTTGGG | 2250 |
| TAAAGCTACA CCTCAAAATA AGGCCTTATA AGATATGTAA TATATTGTTA | 2300 |
| TAAAGAGTTT AACTATAATG ATAATATTTG CCTAGAAAAT CACTTGAAGG | 2350 |
| CCACAGGACT GAAAATTAAT GACAACAAAC ATGATAACTC TACAATTCAC | 2400 |
| TCAAAAGGCA AGGCACACTT GGAAATTATA TTGGAGACAT GGCTTAGTGG | 2450 |
| GGGCATTACT AAAAAATGTC AAGCTGATAC CACTCAAATC TCAACCCTCT | 2500 |
| ACAGGGCGAC TCTATAGGTT TGAGTAATGA CTATAAAAAT CACTTTAAGT | 2550 |

| | |
|---|---|
| GACTGTAGTC AGATTCTGTA TATTAAGTGC AACGGTTTCC TCAAAAGTTT | 2600 |
| TGAGTAATGA CAGCATATTG GGGTTTACAA TGTGGTTATT ATCTTCCACT | 2650 |
| GACATGAAAG TGAAATACAA CTATGCTTTC CTAGTTAGAA AATGCATGTG | 2700 |
| TCTTTTTCTA TATGTGCTTG TAGAATGGCC AAATAAACAA GTATTGATAT | 2750 |
| GCACACATCC ACCCCACCAT GCATCTCTCT CTGTCTCCCA CAGGGGAGCC | 2800 |
| AGGAAGGCAT ACTGAGCCTG GATGACAATG ACTCTCAGCA TCTGCCCCCC | 2850 |
| TACGGGAACT ACTACCAGAA CCTGGGGGGC GACGGCAACG TCAGGAGGAA | 2900 |
| CTACGAACTG TTGGCCTGCT TCAAGAAGGA CATGCATAAG GTGGAAGATC | 2950 |
| ATGTTGCCTT CAATTGCATG TGCCTTCCTA TATTTTCTAC AGTGCATTGT | 3000 |
| TTTTTTTTGT GATCTCTATT GTGAAGTATC TTTGAGTCTT CAACCCATAT | 3050 |
| GTTATTACTA TTATTGTTCA TTGATCAAGA CTGGTCTCGA GAAAGTCCTG | 3100 |
| GTGACTTAGA ACATGCACAT TAAAATGTGT CAACTAATAA CCTATTCTTC | 3150 |
| TTGTCCCAAG GTTGAGACCT ACCTGACCGT CGCTAAGTGC AGGAAGTCAC | 3200 |
| TGGAGGCCAA CTGCACTCTG TAAACGTGGG CCGGAGTGGC AGCCAGCAAG | 3250 |
| AGCCTGTCTC CAGGGTTCGG TTCCCCAGAT ACAGATGAGA CCTTGCCCTG | 3300 |
| CACTGAAGAG CATGTTCAAC TGGGATTCTC CATTAGGCAT GCTTTTTTTA | 3350 |
| GTCTAGATTT CATTTGGATC TGGTAGAGCC TGGCTCCAGG GGTTTTCAAG | 3400 |
| CATTTTGCAT TTTTGTTCTC TGAAATCAAC TTTCTATGAT TTTCACTCCA | 3450 |
| TTACTCGGAG CTACCACTGA TCCATGGACA TTTTAGATTA GTACATTTAT | 3500 |
| AGAAACGGTT TATAAATATG TCTTATTTAG ATATATGATT CAAGGTGGTG | 3550 |
| GTGCCATTTA TGTATAAATT AATATTTAGG GGTGAGATGG GAACATGTAG | 3600 |
| AGCTCCAATC TTTAGGTATG TCCACAGATG GATAATATAA ACGTATTTTC | 3650 |
| ATTCCTTTAT CTTACTGTTT GAAACGAATA GTGATTTGTT TTCAATAAAC | 3700 |
| TTCTCTGCAG TATATGATCT CTTGGCTACT ATTTGCTATC TTTCAAATCA | 3750 |
| ACATTTTTTT TACAAGTTTC TAGCCCCAAC ATTCCTATTG TGTCCCTTGG | 3800 |
| ACAACTTAAG GCTGGATTTA ATTCTTATCG CAGATGCTCC ATTGAAATGT | 3850 |
| CAAGGCAGTG TTCCCTGCGT TC | 3872 |

(2) INFORMATION FOR SEQ ID NO:5:

(i) SEQUENCE CHARACTERISTICS:
        (A) LENGTH: 4706
        (B) TYPE: nucleic acid
        (C) STRANDEDNESS: single
        (D) TOPOLOGY: circular (ix) FEATURE:
        (A) NAME/KEY: enzyme sites and signal sequence
        (B) LOCATION: 1-6    for EcoRI
            325-330 for BamHI
            4084-4089 for XbaI
            4391-4396 for Poly-A (xi) SEQUENCE DESCRIPTION: SEQ ID NO:5:

| | |
|---|---|
| GAATTCCTGA TTAAGTTTTG TATAGTTAAA TAAATATAGG TGTAGCCTTA ATTAATCGAT | 60 |
| GATCAACGTG GTAATCAGGT TTATGTAACA GGCTATGGAA TTTGGAAACA ATAGGAAACT | 120 |
| CTTCCTTGAT TATTTTCGCG CAGTATAATG AAATAACCCG GGTGCAAACC CTGATCGTCT | 180 |
| GAACGCGAGA CTGTTTTGCA CACGGCACCC GTCTGTCCCT GACGCTATAA AAACGGTCTT | 240 |

```
CGCCAAAGAG AAATTTAAAG CTTACAACTC AACAGTGAAA TTGAGCTGAA ATACTTCATT    300

TGACTAAAGA AGCGCGATCG AAAAGGATCC CCATCCTTGG CAATTAAGAG TAAAAATGGG    360

ACAAGGTAAG CCTGCTTTTT CTGTATATTT CTTTTTTCAG TGGGAAGTCA GTGTACCATT    420

TAGTACAATT TAACTAACTG CTATGAGGTT ATAATCTATT GACACAGAAC AACCTGCTTT    480

AACAACCTAA CTATGTGATC AATAACATTT ACATTTGAGT CATTTAGCAG ACACTCTTAT    540

CCAGAGCGAC TTACATGAGC AATTGGGGTT ACGTGCCTTG CTCAAGGGCA CATCAGATTT    600

CTCACCTAGT CAGCTCTGGG GTTGAAACCA GTAACGACCC AGCGCTCTTA ACCCGCTAGG    660

CTATTGGTGT ATGATGGCTG AGAAAATCTT ACTAATGTAT CTCACCATAA TTCGACTTAC    720

TCGTTTTCTA CATTTCTTAT TTGAATCTCT CTTTTAGTGT TTCTGCTGAT GCCAGTCTTA    780

CTGGCCAGTT GTTTCCTGAG TCAAGGGGCA GCGATAGAAA ACCAACGGCT CTTCAACATC    840

GCGGTCAGTC GGGTGCAACA TCTCCACCTA TTGGCTCAGA AAATGTTCAA TGACTTTGTA    900

AGACAGCTTT TGAATCTTCT TTGGACATAT CAAATAGTGT ATCAATGATT GTTCTTCTTC    960

TTGTAGACAG TGTCCTCTTC ACACAACCCT CGTGGCTAAA AAATCTCTC TCTCCCTTTG    1020

TGATTTTGTG CAGGACGGTA CCCTGTTGCC TGATGAACGC AGACAGCTGA ACAAGATATT    1080

CCTGCTGGAC TTCTGTATCT CTGACTCCAT CGTGAGCCCA GTCGACAAGC ACGAGACTCA    1140

GAAGAGTTCA GTAAGTAACC TGGCTGAGAC AATTACGCAT GTTATGCCCT GTAAAGTGTC    1200

AAATCGTGAC AGTTCCACTC TGCTATTCAC CTTAAATATG AACTCCTCCA TGATGCAAGA    1260

TTCCAAAAAT AAATAATAGG GCATCTCAAT TTGAACAATC GATAGAACTT AGTCATTAGT    1320

TATTGGGCAA GCAGACCACC AATTATGTCA ACTCAAATTT ATAATTTTTT ATTTAAATTT    1380

TATTTGAACC TTTAATTAAC TTGGCAAGTC AGTTAAGAAC AAATTCTCAT TTACAATGAC    1440

AAGCAGAGGC AGCATCATGC ATGGCTCTCG AGTGGCACAG CAGTCTAAGG CACTACATCT    1500

CAGTGCCAGA GGCATCACTG CAAACCCTGG TTTGATTCCA GACTGTATTT CAAGCGGCTG    1560

TGATTGTGAG TCCCATAGGG CGGCACACAA TTCTCCCAGC GTCGTTAGGG TTAGGGTTGC    1620

AATACCTCAG TGTTTTTCAA CTAAGGTAGA TAAAACAACC ACATATCATT GCAAGTAAAA    1680

CCATCACTGT CTAATCGGTG GTTTCTCTAC GTCTACATTC TCTGTTTTGT GCTTTTCTGT    1740

ACAGGAAACC CGCCCCAAAA GTATTTCACT CAATCATGTA AATAGGGCAT CTCAAGCTGT    1800

ACAATACAAC TCAACTTAAT TTTCCAATAA TCTGTGGTTT CTCTACATCT TCACACACAG    1860

GTCCTGAAGC TGCTCCATAT TTCTTTCCGT CTGATTGAAT CCTGGGAGTA CCCTAGCCAG    1920

ACCCTGATCA TCTCCAACAG CCTAATGGTC AGAAACGCCA ACCAGATCTC TGAGAAGCTC    1980

AGCGACCTCA AGTGGGCAT CAACCTGCTC ATCACGGTAA AGAAAGGAGG GAGAACAATG    2040

ACCATTTGTG GTGTCACACT TTGTGCACTG TAAACTCCAA GGCATTTTTA ACTCAAATAC    2100

TTCTAGTGAG TTGAACTCAA AGTCAATGAA AAATCCTTAT TGCTTAAAAT GTTTATGTGG    2160

TACTGGCTCA AAACTAAATG AGAAGTCACA TCAATGCAAT TTTTTAAAGT TATAACAAAT    2220

TCACTTTTAC CAAGCATGCT CTACTGCAGG TAGAATTTTT AAAAAAAAAG TTTTTAACGA    2280

TCTGTGTTTT TGCATGTACA GAACATTGAG TGATTGATTC ATTTTATGCT ACACAAAGAA    2340

ACATAACATA CGTTTCAACG TTTTCACAAA GATTAACAAG TCACCAGAAT TCTGCAAACT    2400

CAACTTGCAG GCCTGATGTG GCCTGTATAC CATGAGTTTC AGGCCACTGT ATTAGGGTAA    2460

AGCTACGCCT CAAAATAAGG TCTTATGAGA TAAGTAATGT ATTGTTGTAA AGAGCTGAAT    2520

TATCATGATA ATATTTGCCT AGGAATTCAC TTGAAGGCCA CAGGACTGAA AATGAATGAC    2580

AACAGCCATG TCTCTGTCAC TAACATATAC AGTCATGGGT GATAACTACA CTTCACTCAA    2640
```

```
AAAGGCCAGG CACACTGGGA AATTATATTT GAGACGTGGC TTAGTGGGGG CATTACTAAA      2700

AAATGTCAAG CTGATACAAC TCAAATCTGG ACACATCACA GGGTGACTCT ATAGGTTTGA      2760

GTAATGACTG ACTATAACAT CACTTTAAGT AACTGCAGTC AGATTCTGTA TATTAAGTGC      2820

AACGGGTTTC CTAAAAAAGT GTTGAGTAAT GGCAGCACAT TGGGGTTTGC AGTGACATGA      2880

AAGGGAAATA TCTGTATGCT TTCCTAGTTA GAAAGCATAG TGTAGGACCA CGTATGCCTC      2940

TTCTCAGCAG ATCTTTCAGG GCTTTACATT GTGATGTGGT AACTGACCTT ATCTATCATC      3000

GTGATTGTAT CAGTGACACC CCATTCAATG ACTGAATATC GCCCCATTCA AGGACATTTA      3060

TGCATGTGTC TTTTGCTACG TGTGCTTTCA GAAAGGCCCA ATAAGCAAAT ATTGATATGC      3120

ACACATCCAC CCCACCATGC ATCTCTCTCT GTCTCCCACA GGGGAGCCAG GATGGCGTAC      3180

TGAGCCTGGA TGACAATGAC TCTCAGCACC TGCCCCCCTA CGGGAACTAC TACCAGAACC      3240

TGGGGGGCGA AGGAAACGTC AGGAGGAACT ACGAGTTGTT GGCTTGCTTC AAGAAGGACA      3300

TGCACAAGGT GCGCAACCAT GTTGCCTTCA ATTTCATGTG CCTTCCTGTA TTTTCTACAG      3360

TGCATTGTTT TTTTGTGTTC TCTATTGCAA AGTATTGTTA GTAAATAACT CACGGACACT      3420

AGAGAAGCTT TAACCAAGTT TAATTCTTCC CAAAGGTTCT GTACAGCTGT AATCAGACAG      3480

CAAAACATTT CACTCCACAG TCATATACAT CCTACTTAAA ACACTCCTTC TTCAATCCTT      3540

ATAGTTTATG GCTCCACAGG AAGCTAATAA AGAGGGTAAC AGGACAACAA ACCTTTATTA      3600

CTGCCTTCAG AGAATCTGTC CTCACCTCCT GACCTCAACC CCTCATCTAA TCCACAGATG      3660

TCCATTGTTT TTTTCAGAGA ACCATTAAGT TCTGACATAA CCCAGTTTCT TTCATTTACT      3720

ATCTCAATGA TCAACGTTTA GCCAATTCCA ACAGTATCTT TGGGACTTTA ACCCATATAT      3780

TACTATTATT GTTCATTGAT CAAGACTGTT CTCGAGAAAG GTCTGGTGAC CTAGAACACA      3840

CACATTAAAA TGTGTCAACT ATAACCCATT CTTTTTCTTT TTTCCCCCCC CGAGGTCGAG      3900

ACCTACCTGA CCGTCGCCAA GTGCAGGAAG TCACTGGAGG CCAACTGCAC TCTGTAGACG      3960

TGGGCTGGAG AGGCAGCCAG CAAGAGCCTG TCTCCAGGGT TCGGTTTCCC ATATACAGAT      4020

TAGGCCTTGC CCTGCACTGA GGTGCATTTT CAATTGAGAT TCTCCATTAA ACATGCTTTT      4080

CAGTCTAGAG TAATTTTATT TTGTATCTGG TAGAGCCTGA CTCCAGGAGT TTTCAGGCAT      4140

TTGCATTTTT TTCTCTGAAA TCAACAACAA CACTTTCTAT ATTGACTCTA TCACTCTGAG      4200

CTACCATTGA TTAGTACATT TATAGAAAAG GTTATTACAT GTGCTACTGT TTATGCATAT      4260

GTTAATATTT AGGGGTGAAA TGGGAACTTG TAGAGCTCCA AGCTTTTGGA TAATATATTT      4320

TAGAGTAATT TCCTTTTAGT ATTTTCATTC CTTAATCTTA TTGTTTGAAA CTAATAGTGA      4380

TTCATGTTTC AATAAAGATG TTCTTCTCTG CAGCACATGA TCTCTTGGCT TCTATTTAAT      4440

ATCTTTCAAA TCAACATTTT TTACAAGTTC CTAGCCCCAA CATTCCTATG ATGTCTCTCG      4500

GACAATTTAG GGCCTGGATT CAATCCGTAT CGCAGACGCT CCATTGAAAT GTAAAGGCAA      4560

TGTTCCTGCG TTCGCGGAGA CTGCATTCAC TTCAAACGCT GCTGCATATG TCGGCTCAAT      4620

CGGAAATAAC CTGAAAAATG TTACACGGTT CTTCAGCGAT ACGGATTGAA TCCAGCCCAT      4680

AGTTACGTAC ATTTGTATTG GCAAAA                                          4706
```

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:6:

GGATCCAAGC TTGGCCACCC GGGCCGAATT CTAGA                35

(2) INFORMATION FOR SEQ ID NO:7:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (xi) SEQUENCE DESCRIPTION: SEQ ID NO:7:

AATAAA                6

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

CTGATTAAGT TTTGTATAGT                20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

GTTAAATTGT ATTAAATGGT                20

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

GTCAGGATCC CATCCTTGGC AATTAAGAGT                30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:11:

GTCAGGATCC CATCCTTGGC AATTAAGAGA                30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:12:

-continued

```
GTCAGAATTC ACTGAACTCT TCTGAGTCTC                               30

(2) INFORMATION FOR SEQ ID NO:13:

(i) SEQUENCE CHARACTERISTICS:
          (A) LENGTH:  30 base pairs
          (B) TYPE:  nucleic acid
          (C) STRANDEDNESS:  single
          (D) TOPOLOGY:  linear (xi) SEQUENCE DESCRIPTION:  SEQ ID NO:13:

GTCAGAATTC ACCGCGATGT TGAAGAGCCG                               30

(2) INFORMATION FOR SEQ ID NO:14:

(i) SEQUENCE CHARACTERISTICS:
          (A) LENGTH:  30 base pairs
          (B) TYPE:  nucleic acid
          (C) STRANDEDNESS:  single
          (D) TOPOLOGY:  linear (xi) SEQUENCE DESCRIPTION:  SEQ ID NO:14:

GTCAGGATCC AGCCTGGATG ACAATGACTC                               30

(2) INFORMATION FOR SEQ ID NO:15:

(i) SEQUENCE CHARACTERISTICS:
          (A) LENGTH:  30 base pairs
          (B) TYPE:  nucleic acid
          (C) STRANDEDNESS:  single
          (D) TOPOLOGY:  linear (xi) SEQUENCE DESCRIPTION:  SEQ ID NO:15:

GTCAGAATTC CTACAGAGTG CAGTTGGCCT                               30

(2) INFORMATION FOR SEQ ID NO:16:

(i) SEQUENCE CHARACTERISTICS:
          (A) LENGTH:  29 base pairs
          (B) TYPE:  nucleic acid
          (C) STRANDEDNESS:  single (part of double)
          (D) TOPOLOGY:  linear (xi) SEQUENCE DESCRIPTION:  SEQ ID NO:16:

GATCCAAGCT TGGCCACCCG GGCCGAATT                                29

(2) INFORMATION FOR SEQ ID NO:17:

(i) SEQUENCE CHARACTERISTICS:
          (A) LENGTH:  29 base pairs
          (B) TYPE:  nucleic acid
          (C) STRANDEDNESS:  single (part of double)
          (D) TOPOLOGY:  linear (xi) SEQUENCE DESCRIPTION:  SEQ ID NO:17:

GTTCGAACCG GTGGGCCCGG CTTAAGATC                                29
```

TRANSGENIC FISH AND VECTORS THEREFOR

FIELD OF THE INVENTION

This invention relates to transgenic fish, to promoter and terminator sequences and combinations thereof in vectors, for preparing such fish, and to certain fish growth hormone (GH) genes. It has been found advantageous to insert and express such genes in species of the family Salmonidae, especially coho salmon (*Oncorhynchus kisutch*) and Atlantic salmon (*Salmo salar*).

BACKGROUND AND PRIOR ART

Growth stimulation in animals is expected on the basis of GH protein injection experiments. It has been recognized that the insertion of growth hormone (GH) genes into fish to form transgenic fish should lead to increased growth for such fish. Using mammalian or viral promoters and mammalian GH genes some success was achieved forming transgenic fish in the prior art. However expression of the GH gene was inconsistent and increase in growth was very limited.

The solution to this problem of adequate expression of the transgenes appears to be the identification and thorough characterization of suitable homologous fish promoters for gene transfer involving fish species. "Homologous" is used herein to mean relating to the same fish genus or family. Only a handful of fish promoters have been analyzed for their transcriptional activity using a fish tissue culture or transgenic system. They include the promoters from carp beta-actin; Xiphophorus MT and Xmrk proto-oncogene and oncogene; ocean pout, wolffish, sea raven and winter flounder anti-freeze protein; yellowtail alpha-globin; rainbow trout MT-B; and chinook salmon prolactin. There is clearly a need to increase the pool of well-characterized regulatory DNA sequences that are suitable for gene transfer in fish.

In patent application PCT/CA92/00109, C. L. Hew et al. (published as WO 92/16618 Oct. 1, 1992) there are described gene sequences derived from ocean pout antifreeze gene promoter and other fish gene sequences including chinook salmon GH gene. Gene transfer of this GH gene to form transgenic Atlantic salmon (*Salmo salar*) is disclosed. Some evidence is presented in this reference for increased growth rate and earlier smolting for the transgenic Atlantic salmon. Further aspects of this work are described in S. J. Du et al. Bio/Technol. Vol. 10 pp. 176–181 (1992).

Transgenic fish vectors which consist of the carp β-actin or the rainbow trout metallothionein (MT) promoters and the gilthead seabream GH cDNA are described in B. Cavari et al. Fish Physiology and Biochemistry Vol. 11 No. 1–6 pp. 345–352 (1993). In the above referenced studies all or part of the construct was derived from non-homologous genus of fish.

For the highest assurance of acceptance by regulatory authorities and the public, transgenic fish should have all inserted DNA sequences derived from the same fish genus or family.

In order to increase the commercial potential for the application of transgenics to the aquaculture of Salmonidae, it would be significant to provide promoters, vectors and vector-gene constructs homologous to the family Salmonidae.

SUMMARY OF THE INVENTION

This invention includes a promoter sequence, for use in preparing a gene construct for incorporation into the genome of fish, comprising a nucleotide sequence including the promoter sequence substantially as occurs in sockeye (*O. nerka*) metallothionein MT gene and sockeye histone H3 gene.

The invention covers a transcription terminator sequence, for use in a gene construct for incorporation into the genome of fish, comprising the terminator nucleotide sequence substantially as occurs in sockeye (*O. nerka*) growth hormone GH Type 1 or Type 2 gene.

The concept of combining a promoter sequence selected from an MT gene promoter and a histone H3 gene promoter, with a terminator sequence from a different gene, all such genes being from the same fish genus, is believed unique in a vector or gene construct and leads to more significant levels of transgene expression in fish.

In a preferred aspect, the invention includes a vector or gene construct where there is, in combination, (i) a promoter sequence selected from an MT gene promoter and a histone H3 gene promoter, said promoter being from a species of the family Salmonidae; and (ii) a transcription terminator sequence from a GH gene from the same family as in (i).

The invention further includes transgenic expression vectors with homologous promoter/transcription terminator sequences, for use in preparing a gene construct for incorporation into the genome of fish, comprising in combination (a) a promoter sequence as occurs in Salmonidae, preferably sockeye as described herein;

(b) an intermediate sequence, having at least one selected restriction enzyme recognition site; and (c) a transcription terminator sequence as occurs in Salmonidae, preferably sockeye (*O. nerka*) GH Type 1 or Type 2 gene.

Also included in the invention is a gene construct for incorporation into the genome of a fish, comprising the homologous promoter/transcription terminator sequence as described herein, in combination in sequence (b) with a desired gene sequence to be expressed.

The invention includes a fish gamete cell transformed with the vectors or constructs described herein, and the resulting transgenic fish.

Further included is a method of inducing at least one of accelerated growth and early smoltification in fish comprising insertion of the GH gene DNA construct as described herein into the genome of the fish.

The invention also includes the process of preparing transgenic fish comprising transforming a fish egg with an expression vector including in combination in the vector homologous fish metallothionein MT gene promoter DNA sequence, and homologous fish gene terminator DNA sequence.

Preferably both the MT gene promoter and the gene terminator are substantially as occur in the genome of the homologous fish (which is most preferably the transgenic fish also).

As another aspect of the invention, it has been found advantageous to microinject the vector into the blastodisc region of an egg of the fish, in preparing transgenic fish.

DESCRIPTION OF DRAWINGS AND TABLES

SEQ ID NO:1 depicts the promoter region of histone H3 gene for sockeye (*O. nerka*). The sockeye H3 promoter has 509 bp as shown.

SEQ ID NO:2 depicts the promoter region of metallothionein MT-B gene for sockeye (*O. nerka*). The sockeye MT-B promoter has 318 bp as shown.

SEQ ID NOS:3 and 4 depict the nucleotide sequence of Type 1 and Type 2 growth hormone genes from sockeye salmon. The sequences for the same two genes are shown in an aligned format in Table 1 with the nucleotide position shown at the right margin of each line starting at +1 for the putative transcription start site. The sequences in Table 1 are broken up into promoter, exon, intron, and terminator regions, with protein coding regions in capital letters and non-coding regions shown in lower case. Identical nucleotides between the genes are separated by a |, and gaps inserted in the sequence to improve the alignment are shown by dashes, -. Features such as transcription signals and homologies to various repetitive elements are shown in bold.

SEQ ID NO:5 depicts the nucleotide sequence of pOn-MTGH1 as in Example 3.

SEQ ID NO:6 depicts the polylinker nucleotide sequence shown in FIG. 1A.

Table 2 summarizes the growth performance and serum GH levels of transgenic and control coho salmon (see Example 4).

FIG. 1A is a diagrammatic representation of the pOVMT/GHIT transgenic fish expression vector containing the sockeye metallothionein-B (MT-B) promoter fused to the sockeye Type 1 growth hormone (GH) terminator gene region. Thick black lines represent polylinker sequences from plasmid Bluescript II™; the open box represents the MT-B promoter; the partitioned stippled box represents the GH1 terminator region. The restriction enzyme sites located within the polylinker region are: BamHI, HindIII, BalI, SfiI, EcoRI, and SbaI. KpnI and NotI are located within the plasmid Bluescript II KS-. The poly-A addition site is indicated by AATAAA (SEQ ID NO:7).

FIG. 1B is a diagrammatic representation of the pOn-MTGH1 gene construct containing the sockeye salmon metallothionein-B (MT-B) promoter fused to the sockeye salmon Type 1 growth hormone (GH) coding and terminator gene regions. Thick black lines represent polylinker sequences from plasmid Bluescript II; the open box represents the MT-B promoter; thin lines represent GH1 introns; filled boxes represent GH1 exons; the partitioned stippled box represents the GH1 terminator region. The restriction enzymes sites depicted are: A, ApaI; B, BamHI; K, KpnI; X, XbaI; N, NotI, and the number of nucleotides between sites are indicated above these labels. The poly-A addition site is indicated by AATAAA. Oligonucleotide primers used for screening the transgenic fish by the polymerase chain reaction are represented by labelled arrows. Primer 1 represents oligonucleotide MT-1 from the MT-B promoter (5'-CTGATTAAGTTTTGTATAGT- 3') (SEQ ID NO:8), and the primer 19 represents oligonucleotide GH-19 from intron A of the GH1 gene (5'-GTTAAATTGTATTAAATGGT-3') (SEQ ID NO:9).

DETAILED DESCRIPTION

Figure 1A:
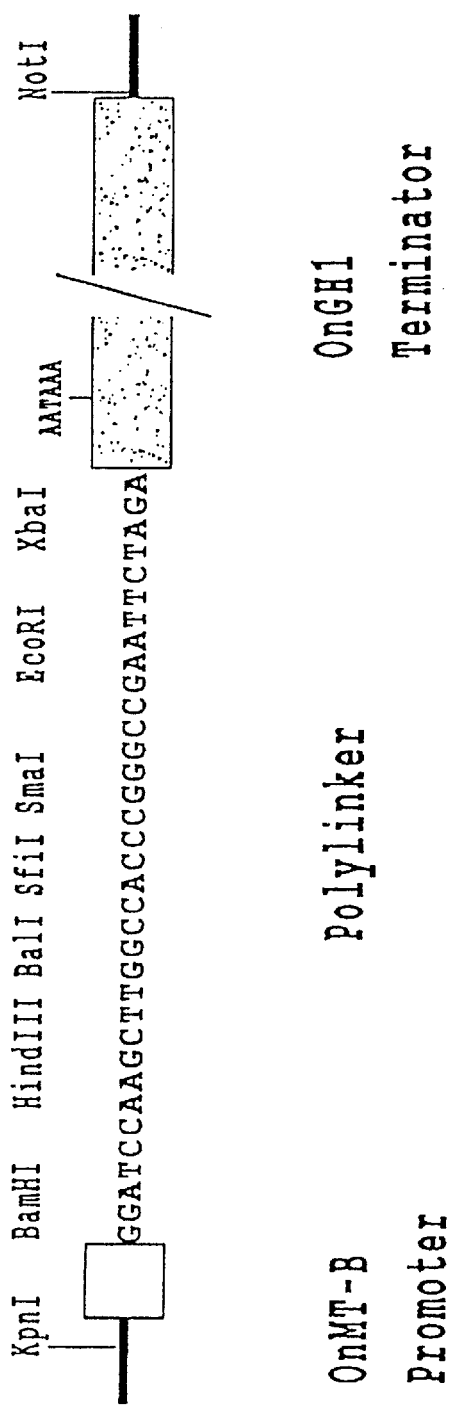

In order to prepare an appropriate vector for making transgenic salmon it was necessary to isolate and identify promoters from the salmon genome. Primers were sought which would enable amplification by polymerase chain reaction (PCR) of selected promoters from sockeye. It was found that primers derived from the nucleotide sequences of rainbow trout promoters could be used to clone corresponding promoters from sockeye. Primer design, PCR cloning, and sequence analysis of histone H3, metallotheonein MT-B and protamine PT promoter sequences from sockeye were carried out as outlined in Example 1 below. The promoter sequences for the sockeye H3 and MT-B promoters are given in SEQ ID NOS:1 and 2. The protamine PT promoter was found to be significantly less active than the H3 and MT-B.

Two types of growth hormone genes have been found in sockeye and their nucleotide sequences determined. The genes encode proteins of 210 amino acids and show similarity to growth hormones characterized from other salmonids. The two sockeye genes are highly conserved in their coding regions and diverge about 18% in non-coding regions. The genes were obtained by constructing a sockeye genomic—DNA library and GH-containing phage were identified both with PCR using primers designed from consensus salmonid GH sequences, and with hybridization using a trout cDNA for GH. Selected fragments from restriction enzyme cutting were subcloned into vectors and a series of deletions and oligonucleotides were constructed to allow DNA sequencing of the putative GH clones in both orientations. Illustrative details are given in Example 2 below. The sequences of sockeye GH Type 1 and 2 genes are given in SEQ ID NOS:3 and 4, and TABLE 1. The terminator portions of the sockeye GH genes were identified as shown.

In order to prepare suitable vectors for transforming host cells, the promoters (H3 or MT) and the terminators (GH1 or GH2) may be each combined so that the promoter and terminator are adjacent, and a selected polylinker, having a selected restriction enzyme recognition site, inserted between them and the three units cloned. The GH gene (or other suitable sequence) is inserted by opening the polylinker with the appropriate restriction enzyme, providing the gene with the matching end sequences, and ligating to form the gene construct.

Plasmids for use in forming the vector may be selected from those having the ability to multiply in bacterial or like cells. Suitable examples are pBluescript II™, pUC18 and pUC19. Still others will be evident to those skilled in the art (see references under "Background and Prior Art" above). Any suitable polylinker having at least one recognition site and appropriate ligatable end sequences may be used.

While the sockeye vector is of particular interest for use in salmonids, particularly Oncorhynchus and Salmo, it is expected that the vector and construct will be broadly applicable in many fish genera.

To prepare transgenic fish, fish cells are microinjected with the vector carrying the gene or DNA sequence to be expressed. While any cell or gamete may be used, we have found it preferable to microinject an egg of the fish to be genetically altered and most suitably the blastodisc region. A suitable procedure is detailed in Example 3B. Transgenic fish are grown from the transformed cell using known techniques.

While one objective is to insert GH genes into fish, especially of the salmonid genus, other genes and DNA sequences may be inserted into the homologous vectors described herein. Preferably the gene or other sequence is homologous with the promoter and terminator.

Growth data on members of two salmon genera of the family Salmonidae (GH transgenic Oncorhynchus and Salmo) and smoltification data are given below in Example 4.

The following examples are illustrative.

EXAMPLE 1

Sockeye Promoters

In order to carry out PCR cloning and sequence analysis of promoter fragments from sockeye, operative primers are required. Tests using primers based on nucleotide sequences of rainbow trout promoters to clone, by PCR amplification, corresponding promoters from sockeye, a related Oncorhynchus species, were conducted. The H3, MT-B and PT gene promoters were investigated.

The design of the H3-1 and H3-2 primers was based on the nucleotide sequence of the rainbow trout histone H2A-H3 intergenic region (W. Connor et al., J. Mol. Evol. 20:236–250, 1984). The H3-1 primer contained the last 20 nucleotides of the histone H2A coding region while the H3-2 primer contained the last 20 nucleotides immediately upstream of the ATG codon of the H3 gene. The amplified fragment would contain the terminator of the H2A gene and the promoter of the H3 gene.

Genomic DNA from sockeye salmon and rainbow trout were subjected to 30 cycles of PCR amplification with the H3-1 and H3-2 primers. A single 529 bp fragment was obtained for the sockeye salmon, which is similar in length to the published rainbow trout H2A-H3 intergenic region. For rainbow trout, two additional fragments (532 and 517 bp) were obtained besides the original 521 bp histone H2A-H3 intergenic fragment reported by Connor et al. The presence of H3 promoter variants is to be expected as the haploid rainbow trout genome contains approximately 150 copies of the H3 gene (W. Connor et al., J. Mol. Evol. 20:227–235, 1984).

PCR primers based on the nucleotide sequence of the rainbow trout MT-B (tMT-B, Zafarullah et al., Mol. Cell Biol. 8:4469–4476, 1988) promoter were used to amplify the sockeye salmon MT-B promoter. The MTB-1 primer included the first 20 known nucleotide sequences of the 5' region of the tMT-B promoter. The MTB-2 primer contained the 20 nucleotides immediately upstream of the ATG codon of the MTB gene. We amplified a 336 bp sockeye salmon MT-B (OnMT-B) promoter fragment using the MTB-1 and MTB-2 primers. Standard PCR techniques were used as described elsewhere.

The nucleotide sequences of the sockeye salmon promoters were determined by the dideoxy chain termination method (see SEQ ID NOS:1 and 2).

The number of base pairs in the MT Type-B gene promoter sequence was found to be 318, and in the histone H3 is 509.

The sockeye histone H3 and metallothionein-B gene promoters were found active in various transfected fish cells but not the sockeye PT promoter. It was concluded from fish cell line tests that the OnH3 and OnMT-B promoters were likely to be active in various tissues from related Oncorhynchus and other fish species and would function as constitutive promoters. In the three salmonid cell lines, the sockeye H3 and MT-B promoters were most active and were used in further tests.

EXAMPLE 2

Sockeye Type 1 and 2 GH Genes

DNA was isolated from the liver of a single male sockeye obtained from Weaver Creek in southwestern British Columbia. A sockeye salmon genomic-DNA library was constructed in the phage vector lambda FIX™ (Stratagene Corp., La Jolla, Calif.) using instructions provided by the manufacturer. The library was plated and transferred to nitrocellulose filters and GH containing phage were identified both with the polymerase chain reaction (primers designed from consensus salmonid GH sequences) and with hybridization with a trout cDNA for GH (Agellon and Chen DNA 5:463–476, 1986). Appropriate restriction fragments were subcloned into Bluescript II™ phagemid vectors and a series of deletions and oligonucleotides were constructed to allow DNA sequencing of the putative GH clones in both orientations.

The primers used in PCR amplification were as follows:

```
GH1  5'-GTCAGGATCC CATCCTTGGC AATTAAGAGT-3'  (SEQ ID NO: 10)

GH2  5'-GTCAGGATCC CATCCTTGGC AATTAAGAGA-3'  (SEQ ID NO: 11)

GH3  5'-GTCAGAATTC ACTGAACTCT TCTGAGTCTC-3'  (SEQ ID NO: 12)

GH4  5'-GTCAGAATTC ACCGCGATGT TGAAGAGCCG-3'  (SEQ ID NO: 13)

GH5  5'-GTCAGGATCC AGCCTGGATG ACAATGACTC-3'  (SEQ ID NO: 14)

GH6  5'-GTCAGAATTC CTACAGAGTG CAGTTGGCCT-3'  (SEQ ID NO: 15)
```

Of $7 \times 10^5$ plaques from a sockeye salmon genomic DNA library that were screened, 17 retested positive for GH sequence and were purified for further analysis. Restriction mapping of these clones revealed the presence of two structurally different classes of genes. The polymerase chain reaction was used to identify those positive clones with homology to oligonucleotides designed from GH genes previously cloned from other salmonids. This approach allowed the identification of two types of full-length genes which differed in the length of fragment amplified between exon 5 and 6. One clone from each of these two gene types was selected for sequence analysis.

A series of deletions and subclones were constructed from each of the two GH gene types to provide starting points for sequence analysis from different positions within each gene. Where appropriate deletions were not available, sequence was extended from oligonucleotides that were designed from sequence obtained in adjacent regions. From this analysis, it became clear that two structurally distinct types of GH genes had been isolated with homology to the Type 1 and Type 2 trout GH cDNAs (Rentier-Delrue et al. DNA 8:109–117, 1989). These two genes were named OnGH1 and OnGH2 ("On" abbreviating Oncorhynchus nerka), and their overall structures and complete nucleotide sequences are shown in SEQ ID NOS:3 and 4 and TABLE 1.

Alignment of the GH gene sequences with cDNA sequences obtained from other salmonids allowed identification of six exons and five introns in both genes (Table 1). The sizes of each exon did not differ between the Type 1 and 2 genes of sockeye and were identical in length to those described for other salmonid GH genes (Agellon and Chen Proc. Nat. Acad. Sci. USA 85:5136–5140, 1988; Johansen et al. Gene 7:317–324, 1989; Male et al. Biochem. Biophys.

Acta 1130:345–348, 1992). The sizes of the different introns differ both between Type 1 and 2 genes of sockeye as well as among the three Type 2 genes isolated to date, and the sockeye Type 1 gene contains an approximately 350 basepair insertion relative to the Type 2 and the Atlantic Type 1 genes. All intron-exon boundaries are flanked by the appropriate splice consensus, /GT . . . AG/, found in many other eukaryotic systems. The overall nucleotide lengths of these two genes from the promoter TATA box to the poly-A addition signal is 4138 for OnGH1 and 3440 for OnGH2. This difference in size is largely due to multiple deletion and/or insertion events present in all introns except intron B. Transcriptional regulatory sequences could be identified in the 5' flanking regions of both genes (Shown in Table 1), including a TATA box and a putative Pit-1 (GHF-1) transcription factor binding site.

The present Example has shown that two distinct genes for GH are present in sockeye salmon, and that both have intact structures expected for transcriptionally active genes. A high degree of conservation is observed between the coding regions of these two genes suggesting that functional constraints have operated to conserve the two proteins. Non-coding regions (introns and terminators) are, as expected, less well conserved between the two GH genes, showing many deletion/insertion events as well as base substitutions. Non-coding gene sequences data consisted of all introns combined with the terminator region from the stop codon to the poly-A addition signal.

Growth hormone genes contain five exons and four introns in all cases examined except for salmonids where there is a fifth intron separating exons 5 and 6. This latter organization has been observed in Type 1 and 2 GH genes in Atlantic salmon (Johansen et al. op. cit.; Male et al. op. cit.), in the type 2 gene of rainbow trout (Aggelon et al. op. cit.) and (in the present Example) for both the Type 1 and Type 2 GH genes from sockeye salmon.

The GH1 and GH2 terminator regions shown have 633 and 651 bp respectively. A group of about 2800 base pairs of the terminators has not been sequenced. The complete terminators have about 3500 bp each.

EXAMPLE 3

Preparation of Vectors and Transgenic Fish
A. Vectors

The vector construct in FIG. 1A was synthesized by cloning a 3450 bp XbaI fragment containing the terminator region of the GH1 gene described in Example 2 into Bluescript II™ KS- to yield plasmid pnGH4.4. The 3' XbaI site (derived from the phage vector Lamda Fix™, Stratagene Corp.) was removed from pnGH4.4 by partial digestion with XbaI, filling the sticky ends with T4 polymerase, ligation, and retransformation to produce plasmid pGH4.4X⁻. The 318 bp MT-B promoter (as described in Example 1) flanked by 5' EcoRI and 3' BamHI sites was generated by PCR and inserted into EcoRI and BamHI sites of plasmid pGH4.4X⁻ to produce plasmid pKARMTBXGH1T. This latter plasmid was digested with EcoRI and ApaI, filled with T4 polymerase, and religated to produce plasmid PKRMTBXGH1T which was digested with EcoRI alone and filled with T4 polymerase and re-ligated to produce pKMTBXGH1T. This plasmid was digested with BamHI and XbaI and ligated to two annealed oligonucleotides (PL-1) and PL-2) having the following sequences:
Oligonucleotide PL-1
5'-GATCCAAGCTTGGCCACCCGGGCCGAATT-3' (SEQ ID NO:16)
Oligonucleotide PL-2
3'-GTTCGAACCGGTGGGCCCGGCTTAAGATC-5' (SEQ ID NO:17)
Clones isolated from this ligation yielded the construct pOVMT/GH1T (Oncorhynchus Vector MT/Growth Hormone 1 Terminator) shown in FIG. 1A.

Figure 1B:
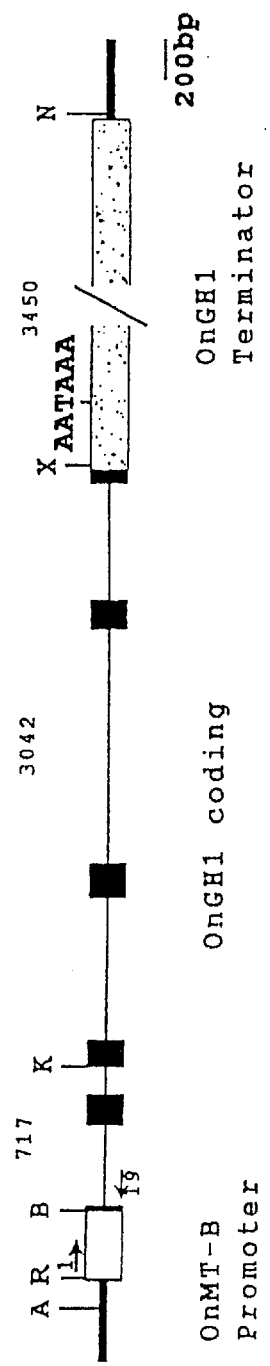

The fusion gene in FIG. 1B was constructed as follows. First, a BamHI (B) site was introduced into the 5' untranslated leader region of the sockeye Type 1 GH gene as follows: PCR from between the 5' untranslated leader region of the sockeye GH1 gene using oligonucleotide GH-1 (5'-GTCAGGATCCCATCCTTGGCAATTAAGAGT-3') (SEQ ID NO: 10) and primer GH-3 in exon 3 (5'-GTCAGAATTCACTGAACTTCTGAGTCTC-3') (SEQ ID NO:12) yielded amplified DNA from which a 717 bp BamHI to KpnI (K) fragment was isolated. This fragment was ligated with a 3042 bp KpnI to XbaI fragment (containing the rest of the GH1 gene) into the salmon promoter-terminator vector pKARMTBXGH1T described above. This vector contained a 318 bp sockeye salmon MT-B promoter separated by BamHI and XbaI sites from a 3450 bp XbaI sockeye salmon terminator fragment containing the GH1 polyadenylation site (AATAAA). The entire fusion gene was isolated for microinjection by digestion from the plasmid with ApaI (A) and NotI (N) and gel purification.

The DNA sequence of pOnMTGH1 is shown in SEQ ID NO:5. The first 4706 bases are shown starting from the introduced EcoRI site at the 5' end of the MT-B promoter. An introduced BamHI site at the junction of the promoter and GH1 gene is shown in feature, as are the initiation ATG, an XbaI site, and the poly-A addition signal. Approximately 2800 bases of terminator DNA of unknown sequence are also present next, followed by the deleted XbaI (XbaI) site and intact SacI and XbaI NotI sites present in the Bluescript II KS- polylinker.

B. Transgenic Fish

The gene construct pOnMTGH1 was microinjected into fish gamete cells as follows.

Linear DNA (the 7.5 kb ApaI-NotI fragment from pOn-MTGH1 dissolved at 100 ug/mL in 1 mM Tris, 0.1 mM EDTA, 0.5% phenol red, pH 7.2) was introduced into fertilized coho salmon eggs whose development was temporarily arrested by maintenance in an iso-osmotic saline solution. The microinjection needle (5 µm tip diameter) was inserted with a micromanipulator through the unhardened chorion and the vitelline membrane into the central blastodisc region (future animal plate region) in the vicinity of both the micropyle and the maternal pronucleus. Approximately 2 nL of DNA solution was introduced using an Eppendorf model 5242 Nitrogen gas injection system. Embryonic development of the injected eggs was initiated by transfer to fresh water (10° C.). Of 3156 eggs injected, 1866 developed to hatching, representing a survival of 69.8% relative to the control hatching success. Salmon were reared in fresh water containing no added metal ions to limit expression from the metallothionein promoter to constitutive levels. Fish were fed to satiation three times a day with a commercially prepared semi-moist diet (Moore-Clarke).

At 12 months post-fertilization, individual fish were tagged and a small piece of adipose fin tissue removed for PCR analysis to determine the persistence of the pOnMTGH1-injected DNA. In the initial PCR screen, 67 transgenic individuals were identified among 1073 surviving salmon examined. Among 24 "fin-negative" fish that were larger than controls, 7 were found to be positive in blood cells. In all, 74 transgenic individual fish were identified representing a frequency of gene retention of 6.9%. This frequency is comparable to reported rates in transgenic mammals and fish produced by microinjection.

EXAMPLE 4

Growth Rate and Smoltification Tests

At 12 months of age (10 months after first feeding) weight and length determinations were made on 1073 surviving individuals (for Example 3B) in the microinjected group; and on 792 individuals in an uninjected control group raised under the same conditions. The results are summarized in Table 2.

The control group displayed a uniform frequency distribution of weight classes typical of coho salmon raised in fresh water conditions, while the microinjected group had the same modal weight as controls but, in addition, contained many larger individuals lying outside of the normal distribution. One of the larger controls weighed 24 g while a few of the larger transgenic fish reached about 500 g. The mean weight of the transgenic group as a whole was about 155 g.

Transgenic individuals were on average more than 11-fold heavier than controls (Table 2), and the largest individual was remarkably 37 times heavier than the mean control weight. In contrast to mammals, salmonids continue to grow throughout their entire life cycle, and even small differences in specific growth rate quickly compound into very large increases in size (Table 2). The dramatic growth enhancement observed in these experiments appears due to the homologous design of the pOnMTGH1 construct, as well as the use of the MT-B promoter with a full-length GH1 gene including introns to increase transcriptional activity. Condition factors (an indicator of weight relative to length) did not differ between control and transgenic salmon (Table 2), suggesting that allometric growth resulted in normal body proportions in most transgenic fish. Some transgenic individuals displayed an overgrowth of cartilage in the head and opercular regions, with the severity and frequency of the morphological abnormality being correlated with larger size. This phenotype may be analogous to acromegaly, a syndrome observed in mammals that arises from elevated levels of GH production. In our experiments, measurement of plasma GH revealed that transgenic individuals had GH levels more than 30× higher than controls (Table 2). These results confirm that the pOnMTGH1 construct was constitutively driving expression of much larger amounts of GH than is normally produced from the pituitary gland.

Coupled with the dramatic effect on size in transgenic salmon was a striking change in external colouration. All large transgenic fish took on a silver colouration and lost the dark vertical bars (parr marks) that are characteristic of juvenile salmonids. This transformation (smoltification) normally occurs in the spring of the second year in preparation for migration from the natal fresh water environment to the sea, and is correlated with a rise in serum GH levels and elevated growth. In our experiments, we have presumably overridden the seasonal control of GH, and transgenic fish underwent smoltification in the later summer and fall of their first year, some six months ahead of schedule. Although the fish in this experiment were not old enough to begin sexual maturation, we have observed that approximately 80% of first generation transgenic salmon containing other gene constructs will transmit the transgene to $F_1$ progeny.

We have demonstrated also that the pOnMTGH1 gene construct can stimulate the growth of Atlantic salmon (*Salmo salar*) in a similar fashion.

The present results obtained with the gene construct in salmon should be more generally applicable for growth and maturation enhancement in other cultured finish species especially cold-water species. Our results indicate that a promoter from a given fish species would be operative with a terminator from any other species of the same fish family although the Salmonidae/Salmonidae combination is preferred.

TABLE 1

DNA seqence of Sockeye Salmon Type 1 and 2 Growth Hormone genes (Aligned)

PROMOTER

```
GH1-tt----cacagactgtattgatcaagtgactcttatgttgtgttgatgataacaagaccctgtctgaatttaacacaaaaactatacattctaac-524
         ||||||||||||||||||||||||||||||||||||||||||||||||||||||||||||||||||||||||||||||||||||
GH2-aaaggctctcacacaaaagaccaaaacgggcattgatcaagtggctgtttatgtttatgtaaac------gaa------caaaagac-atactttgtaag-525

GH1-atgtgcgtc  tcgagtcctc-tctgtgtgtctacttgagg--acttgac-taagtgttaatgccataggacattcaatttgacattaacaataaca-428
       ||||||||||||||||||||||||||||||||||||||||||||||||||||||||||||||||||||||||||||
GH2-atgtgc-gtc  tcaagtcctgataggtccttct-ctgtgtgtctacctgagtctctgctcataccatagacattcaatt-gacattaaacaatcaaa-428

GH1-tattgggttaataaagaagcaatgtaataaatgtcttgtcatactgctgttatctacagtaccacagcggaatgcagaataacctgtgtgtg-cg-329
    ||| ||||||||||||||||||||||||| ||||||||||||||||||||||||||||||||||||||||||||||||||||||
GH2-tattgtgctaataaagaagcaataatatattgtcaa-ataatgctgtcatctacagtaccacagcgggacggcaga-taaccggcgttgttgtca-330

GH1-tgt----gcgcgtgcgtgcgtgtgtgtgtctgtgtgtgtgaacttgtgtccattcattacctctagacaacagaaggtttgttgtatgtgttgaccta-233
        |||||||||||||||||||||||||||||||||||||||||||||||||||||||||||||||||||||||||||
GH2-agtacagggtgtctgtcgtatgactgagtgtaactttgttcattcattatgtcctagacaacagaggtttgtcgtatgtgttgccctc-230

LTR-like repeat (56.3%)
                                        Pit-1
GH1-attcgttcagtcatcaagtaagtagtt-ttttttaggacacctccccctttcccaaactcatgaaaaatgtatgatgatttgacgtaatatggtaattg-134
    |||||||||||||||||||||||||||||||||||||||||||||||||||||||||||||||||||||||||||||||||||||
GH2-atttgtcaagtcatcgagtacgtgttgttgttgttttaggag---tcaccctcccgaactcatgaactcatgaaaaattcatgatcgattgacgcattactgattc-133

GH1-ttccacaatcacatacagaaacaggtcctatcaatgaaaggtggtaaagatgaaatctcatggtcctcctatgtgatacattaaacatggattccc-34
    |||||||||||||||||||||||||||||||||||||||||||||||||||||||||||||||||||||||||||||||||||
GH2-ttccatatgtcacatacaaaacaggtcccatcgcgagaggtgtacatggtgtacatga-gaaatctcatgtgtcctcctgttgatacattaaacatgtattccc-34

TATA Box
GH1-cgtctataaaaacagtggccccaaacaacgac-1
    ||||||||||||||||||||||||||||||
GH2-catctataaaaacagtgcccccaaacaagcggc-1

EXON 1

GH1-aacatactcaaccgacaccgcactttcaagttaagtaac-catccttggcaattaagagtaaaATGGGACAAG 74
    ||||||||||||||||||||||||||||||||||||||||||||||||||||||||||||||||||
GH2-aacatactgaaccgaccgaccaccaccacccaccttttcaagtgaagtaataatcatccttggcaattaagagagagaaaATGGGACAAG 75
```

TABLE 1-continued

DNA seqence of Sockeye Salmon Type 1 and 2 Growth Hormone genes (Aligned)

INTRON A

```
GH1-gtaagcctgctgcttttctgtatatttcttttcagtggaagcagtgtaccatttgtacaattact--aac----------------- 147
         |||||  |  |5    |5   |||       |||||||||||||||||  |||  ||||||  |||
GH2-gtaaaccagctgt------tat--tttattttttaagtgggaagtcagtgtaccattttaactgaacattaatcactgaggcaggagccaa 169

GH1----------------------------------------tgctatgaggttataatctattgacacagaacaacctgctttaacaacctaacta 202
                                            ||||||||||||  ||||||||||||  |||||||||||||| |||||||||
GH2-caaggcagagaaagagtgaactaataattactaatagtaatgtactgccatgagggtataatctacttacacagaaccactcctttaat----taacaa 265

GH1-tgtgatcaataacattacatttgactcatttagcagacacactcttatccagagcgactacatgggttacgtgcttgctcaagggcacat 302
     |||   ||||||||| ||| || ||||||| |||||| | ||||||| || ||||||||  |||| | |||||||| ||||| ||||||
GH2-cgtgatctattaggttacatttgagttagtcagcagacgcgcttcttatccagagcgacttac----agcaattaggttaagtgcttgctcaagggcacat 362
                                                                       SINE repeat (60.0%)

GH1-ca---gatttctcacctagtcagctctggggttgaaaccagtaac---------gacccagcgctcttaacccgctaggctattggtgtatggc 387
     ||    |||||||||||||||||||||||  |||| |||||||||          |||||  |||||||||| ||| ||||||  || |||
GH2-caacagatttctcacctagtcagctcaggattcaaaccagtaaccttcaagctactggctactggctcaacgctcttaatca--ctaggctattgatgtacaaaggc 461

GH1-tgagaaaatcttactaatgtatctccaccataattcgactgactactgcgttttc--tacatttcttatttga----atctctctttttag 466
     |||||| ||||||||||||| | ||||||||||||||||||  |||||||||     |||||||||||||        |||||||||||||
GH2-caacagattcttactaactgtcgcaacataatttgactactgcgtcgtttttataccacatttcttatttttccatctctcttttag 545

EXON 2

GH1-TGTTTCTGCTGATGCCAGTCTTACTGGCCAGTGTTTCCTGAGTCAAGGGGCAGCGATAGAAAACCAACGGCTCTTCAACATCGCGTCAGTCGGGTGCA 566
    ||||||||||||||||||||||||||||||||||||||||||||||||||||||||||||||||||||||||||||||||| ||||| ||||||||
GH2-TGTTTCTGCTGATGCCAGTCTTACTGGCCAGTGTTTCCTGAGTCAAGGGGCGGCGATGGAAAACCAACGGCTCTTCAACATCGCAGTCAGTCGGGTCCA 655

GH1-ACATCTCCACCTATTGGCTCAGAAAAATGTTCAATGACTTT 606
    |||| |||||||||||||||||||||||||||||||| ||||
GH2-ACACCTCCACCTATTGGCTCAGAAAAATGTTCAACGACTTT 685

INTRON B

GH1-gtaagacagctttgaatcttcttgtgacatatcaaatagtgtatcaatgattgttcttcttt--gtagaca--gtgtccttcacaaccctcgtgg 704
    ||||| ||||||||||||||||| ||||||||||| || || ||||||||| ||  ||  ||   |||| |   |||| |||||||  ||||||
GH2-gtaagagacagctttgaatcttctttgaatcttctttgacacacagcagataatgttcagaggttgttcctctcttgtgaggttgtgcctcttcacggaggcgg 785
```

TABLE 1-continued

DNA seqence of Sockeye Salmon Type 1 and 2 Growth Hormone genes (Aligned)

```
GH1-ctaaaaaaatctctctccc-ctttgtgattttgtgcag 742
       ||||||| |||||||||||  |||||||||||||||||||
GH2-c-aaaacattctctctcccgtctttgattttgtgcag 823
```

EXON 3

```
GH1-GACGGTACCCTGTTGCCTGATGAACGAGACAGCTGAACAAGATATTCCTGCTGGACTTCTGTATCCTGAGCCCAGTCGACAAGCACG 842
    |||||||||||||||||||||||||||||||||| ||||| ||||||||||||||||||||| ||||||||||||||||| |||||
GH2-GAAGGCACCCTGTTGCTGTTGATGAACGAGACAGCAGCTGAACAAGATATTCCTGCTGGACTTCTGTAACTCTGACTCTGAGCCCATCGACAAGCAGG 923
```

```
GH1-AGACTCAGAAGAGTTCA 859
    |||||||||||||||||
GH2-AGACTCAGAAGAGTTCA 940
```

INTRON C

```
GH1-gtaagtaacctgctgagacaattacgcatgttatgccctgtaaagtgtcaaatcgtgacagttccactctgtattcaccttaaatatgaactcctcca 959
    ||||||||  ||||||||||||||
GH2-gtaagttaccgggctgagacaat---------------------------------------------------------------cctcca 969
```

```
GH1-tgatgcaagattccaaaataataggcatctcaattgaacaatcgatagaacttagtcattagtcattattgggcaagacagaccaccaattatgtca 1059
    |||||||||   ||||||   ||||||
GH2-tgatgcacaattccaaca-tgaataataggcatccaagtgaacaatcgatacaacttagtcattagttatattgggcaagacagagatccccgattgtctaa 1069
```

```
GH1-actcaaatttataatttttattgaaccttttaattaactggcaagtcagttagaacaaattctcattacaatgacaagcagaggc 1159
    ||||||   |||||||||
GH2-actcca------------atat-----------act----gt-agtaagaagaa---c-------------------------------------c 1106
                                     SINE repeat (49.3%)
```

```
GH1-agcatcatgcatggctctcgagtggcacagtctaaggcactacatctcagtgccagaggcatcactgcaaaccctggtttgattccagactgtattt 1259
    |||||||||||||||
GH2-agcatcatgcatgg-t------------------------ag----aa---attaatct-------agccatgacag-------gg-------ttt 1152
```

```
GH1-caagcgcggctgtgattgtgagtccataggggcggcaccatagggcgcacacaattctcccagcgtcgttaggggttgcaataccagtgttttcaactaaggtaga 1359
    |||||
GH2-taa--------attgt-----------acac--tt------aaaatcggcaggaaaatg--ttgctataccagtccagtgcctt--caa---aca 1212
```

```
GH1-taaaacaaccacata-tcattgcaagtaaaacc-atcactgtctaaattcctactgtctcaattcctgtttttgtcttttctgtacaggaa 1457
    |||
GH2-accacatgt--catagtcctgtaagtaaaacccatcactgtcactctctaatcgcgttttctctactctacattctc------------cagcaa- 1290
```

TABLE 1-continued

DNA seqence of Sockeye Salmon Type 1 and 2 Growth Hormone genes (Aligned)

```
GH1-cccgccccaaagtatttcactcaatcatgtaaataggcatctcaagctgtacaat-acaactcaacttaatttccaataatctgtggtttctctaca 1556
        ||||     |||||  |||  |||   ||||  ||||||||| ||||  |||||||||||||||||||||||||||||||||||||||||||||
GH2---------------tgtgtcatgtaa--atg---atatgcatctcaagctgtacaattacaactcaacttcattttccaataatctgtggtttctctaca 1372

GH1-tcttcacacacag 1569
    |||  ||||||||
GH2-tctacacacacag 1385

EXON 4

GH1-GTCCTGAAGCTGCTCCATATTTCTTTCCGTCTGATTGAATCCTGGGAGTACCCTAGCCAGACCCTGATCATCTCCAACAGCCTAATGTCAGAAACGCCA 1669
    ||||||||||||||||| ||||| |||||| |||||||||||||||||||||||||||||||||||||||||||||||||||||||||||||||||||
GH2-GTCCTGAAGCTGCTCCGTATCTCTTTCCGCCTGATTGAATCCTGGGAGTACCCTAGCCAGACCCTGACCATCTCCAACAGCCTAATGTCAGAAACTCCA 1485

GH1-ACCAGATCTCTGAGAAGCTCAGCGACCTCAAAGTGGCATCAACCTGCTCATCACG 1725
    ||||||||||||||||||||||| ||||||||||||||||||||||||||||||
GH2-ACCAGATCTCTGAGAAGCTCAGCAGACCTCAAAGTGGCATCAACCTGCTCATCGAG 1541

INTRON D

GH1-gtaaagaaggaggggagaacaatgaccatttgtggtgtcacactttgtgcactgtaaactccaaggcatttttaactcaaatacttccagtgagttgaac 1825
    ||||| |||||| |||| |||| |||||||||| ||||||| |||||||||||||    ||||              ||||||||| ||||||||||
GH2-gtaatggt------caattaccatttgtggtgccgcactttgtgca------------tttttaactcaaatacttcctagtaagttgaag 1613
        LTR-like Repeat (52.0%)

GH1-tcaaagtcaatgaaaaatccttattgctaaaatgttatggtactggctccaaaactaaatgagaagtcacatcaatgcaattttttaaagttataac 1925
    |  |||||||||| ||||||||||  |||| ||||| ||||||||||||  ||||||||||||||   ||||||||||||| |||||||||||||||
GH2-tc--agtcaatgaaagtcattattacttccaaatgtctatgtgtactggctccaaatctaaatgag---tcaatcaatgcaattttttaaagttataac 1708

GH1-aaattcacttttt-accaagcatgctcactgcctctactgcaggtagaattttttaacgatctgtgtttttcatgtacagaacattgagtgatt 2024
    ||||| |||||||  |||| |||| ||| ||| |||||||| ||   ||||    ||||| |||||  ||||| ||| ||||||||||||
GH2-aaattaactttttaccccagcacgctctactacggtagattttttgaatt---gttttaat-atctgtgttttttgcatgtacagtacattgagtgatt 1804

GH1-gattcatt--------ttatgctacacaaagaaacataacatacgttt--caacgtttttcacaaagat---taaca----agtcaccagaattctgcaaa 2107
    |||||||        |||||||||||||| ||||||||| ||||||||  ||||||||| ||||||   |||||     |||||||||| ||||||||
GH2-gattcattcattcatcttatgctacacacagatatataacgtacatttctcacatttttcacaaagataaataacatacaaggtactggaatttttgcaaa 1904

GH1-ctcaacttgcaggcctgatgtgcctgtataccatgagtttcaggcactgtattagggtaaactgcctcaaataaggtcttatgagataagtaat 2207
    ||  ||||||||||||||||| |||| ||||||||||||||||||||||||||         |||||||  ||||||  |||||| ||||||
GH2-c--ctacttgcaggcctgatgtgcctgcctgtaaaccatgagtttcaggcactgtatttggtaaagtaagctcaaaataaggtcatatttggtaagatgatgtaat
```

TABLE 1-continued

DNA seqence of Sockeye Salmon Type 1 and 2 Growth Hormone genes (Aligned)

```
GH1-gtattgttgtaaagagctgaattatcatgataatatttgcctaggaattcacttgaaggccacaggactgaaaatgaatgacaacagcatgtctctgtc 2307
       |||||||||||||||||||||||||||||||||||||||||||||||||||||||||||||||||||||||||||||||||||
GH2-atattgttataaagagtttaactataatgataatatttgcctaggaattcacttgaaggccacaggactgaaggccacaggactgaaaatcacttgaaggccacaggactgaaaattaatgacaacaaacatg------- 2095

GH1-actaacatatacagtcatgggtgataactacacttcactcacaaaagccagcacactgggaaattatatttgagacgtggcttagtggggcattacta 2407
       |||||||||||||||||||||||||||||||||||||||||||| |||||||||||||||||||||||||||||||||
GH2------ata-ac--------t---ctacaattcactcacaaa--ggcaaggcacacactggaaattatattgagacatggcttagtggggcattacta 2173

GH1-aaaaatgtcaagctgatacaactcaaatctggacacatccacaggtgactctcataggtttgagtaatgactgactataacatcacttaagtaactgcag 2507
       ||||||||||||||||||||||||||||||||||||||||||||||||||||||||||||||||||||||||||||||||
GH2-aaaaatgtcaagctgatacctgatacctactccaccctctacaggggcactctataggtttgagtaatgacta---ta--aaaatcacttaagtgactgtag 2270

GH1-tcagattctgtatattaagtgcaacggtttcctaaaaaagtgttgagtaatgcagcacattgggtgtgcagtgacacatgaaaggaaatatctgtatg 2607
       ||||||||||||||||||||||||||||||||||||||| |||||||||||||||||||||||||||||||||||| ||
GH2-tcagattctgtatattaagtgcaacgg--tttcctcaaaa-gttttgagtaatgacagcatatattgggttttacaatg---t----ggttattatct---- 2356

GH1-ctttcctagttagaaagcatagtgtaggaccacgtatgcctctctctcagcagatctttcagggctttacattgtgatgtggtaactgacctatctatca 2707
       ||||||||||||||||||||||||||||||||||||||||||| ||
GH2-----tcc--act---gacatgaaagtgaaatacaac-tatgc----------tttc-----ct--------------------- 2394

GH1-tcgtgattgtatcagtgacacccattcaatgactgaatatgccccattcaaggacatttatgcatgtgtcttttgctacgtgtgcttcagaaaggcc 2807
       ||||||||| || ||||||||||||||||||||||||||
GH2----------agttaga---------------aa---------------atgcatgtgtctttttctatatgtgctagaatggcc 2442

EXON 5

GH1-caataagcaaatattgatatgcacaccaccacccaccatgctctctctgtctcccacag 2870
       |||||||||||||||||||||||||||||||||||||||||||||||||||||||
GH2-aataaacaagtattgatatgcacacatcccaccccaccatgcatctctctgtctcccacag 2505

GH1-GGGAGCCAGGATGCGTACTGAGCCTGGATGACAATGACTCTCAGCACCTGCCCCCCCCTACGGAACTACTACCGGAACCTGGGGAAGGAAACGTCA 2970
       ||||||||||||||||||||||||||||||||||||||||||||| |||||||||||||||||||||||||||||||||||||||||||||||||
GH2-GGGAGCCCAGGAAGGCCATACTGAGCCTGGATGACAATGACTCTCAGCACCATCTGCCCCCCCCCCCTACGGGAACTACTACCAGAACCTGGGGGGCGACGGCAACGTCA 2605

GH1-GGAGGAACTACGAGTTGTTGGCTTGCTTCAAGAAGGACCATGCACAAG 3017
       ||||||||||||||||||||||||||||||||||||||||||| |||
GH2-GGAGGAACTACGAACTGTTGGCCTGCTGCTTCAAGAAGGACATGCATAAG 2652
```

TABLE 1-continued

DNA seqence of Sockeye Salmon Type 1 and 2 Growth Hormone genes (Aligned)

INTRON E

```
GH1-gtgcgcaaccatgttgccttcaatttcatgtgcttcctgtattttctacagtgcattgttttttgttctctattgcaaagtattgttagtaaataa 3117
        |||||||||||||||||||||||||  |||||||||||||||||||| |||||||||||||||  |||||||| ||||||||   |||||||
GH2-gtggaagatcatgttgccttcaattgcatgtgcctcctcctatattctcacagtgcattgtttttttgtgatct-----c----tattgt--------- 2734

GH1-ctcacggacactagaagctttaaccagtttaattcttcccaaagttctgtacagtcgtaatcagacagcaaaacatttcactccacagtcatatac 3217
    ||||                 ||||
GH2------gaag--------------------------------------------------------------------------------tat-- 2741

GH1-atcctactaaaacactcctctttcaatcctatagttatgctccacaggaagctaataaagagggtaacaggacaacaaaccttttattactgcttc 3317
                                                                                     ||||
GH2-----------------------------------------------------------------------------------cttt---------- 2745

GH1-agagaatctgtcctcacctcctgacctcaaccctcatctaatccacagatgtccattgttttttcagagaaccattaagttctgacataacccagttt 3417
                         ||||||           ||||||
GH2----gag---tct-----------tcaaccc-------------atatgt----------------------------------------------- 2764

GH1-ctttcattactatctcaatgatcaacgttagccaattccaacagtatctttgggactttaacccatattattacttattattgttcattgatcaagactg 3517
                                                                         ||||||||||||||||||||
GH2----------------------------------------------------------------tattactattattgttcattgatcaagactg 2795

GH1-ttctcgagaaagtctggtgactagaacacacattaaaatgtgtcaacta--taaccccattctttttttccccccccgag 3603
    ||||||||||||||||||||||||  |||||||||||||||||||| ||||||                    ||||||
GH2-gtctcgagaaagtcctggtgactagaacatgtcacattaaaatgtgcaacattaaccaataaccctattct---tcttgt-------cccaag 2872
```

EXON 6

```
GH1-GTCGAGACCTACCTGACCGTCGCCAAGTGCAGGAAGTCACTGAGGCCAACTGCACTCTG 3663
    ||||||||||||||||||| |||||||| |||||||||||||||||||||||||||||
GH2-GTTGAGACCTACCTGACCGTCGCTAAGTGCAGGAAGTCACTGAGGCCAACTGCACTCTG 2932
```

TERMINATOR

```
GH1-tagacgtgggctggagagcagcagcaagagcctgtctccaggggttcggttcccatatacagattaggcctgccctgcactgaggtgcattttcaat 3763
                                                                                       ||||
GH2-taaacgtgggcggagtggcgcggcagcaagagcctgctctccagggtcggtcccccagatacagatgagacctgcctgcactgaagagcatgttcaac 3032

GH1-tgagattcctccattaaacatgttttcagtctagagaatgttctagagcctggtagagccctgactccaggagttt-gcatttt--gcattttt--tt 3861
                                                                              ||||||||   ||||||||
GH2-tggattcctccattaggcatgctcttt---tttgtctagagattctcatttgatcgtagagccctgctagagccctgaagctgagaggagtggggtttcaagcatttcaagcatttttgtt 3129
```

TABLE 1-continued

DNA seqence of Sockeye Salmon Type 1 and 2 Growth Hormone genes (Aligned)

```
GH1-ctctgaaatcaacaacaacacttctatattgactctatcacctgagctaccattgat------------tagtacatttatagaaaggttat 3944
         ||||||||||||||||||||||||||||||||||||||||||||||||||||||||||          ||||||||||||||||||||||
GH2-ctctgaaatcaactt----tctatg-attttcactccattactcggagctaccactgatccatggacatttagattagtacatttatagaaacgttta 3224

GH1-tacat---------------gtgctactg---tttatgcatatgttaatatttagggtgaaatgggaacttgtagagctccaagctt 4014
    |||||                |||||| |     ||||||||||||  ||| |||||||||| | ||| |||||||||||||| |||||
GH2-taaatatgtctattagatatgattcaaggtggtggtgccatttatgtataaattaatatttagggtgagatgggaacatgtagagctccaatctt 3324

Poly-A
GH1-ttggataatatttttagagtaattcctttagtatttcattccttaatctctattgtttgaactaatagtgattcatgtttcaataaagatgttctt 4114
    |||| || |||  ||| ||  |||||   |  |||||||||  |||||||| | ||  || |||| ||| | |||||| ||||||||       |||
GH2-taggtatgtccacagatggataataaac---gtattttcattccttttatctactgtttgaaacgaatagtagtttgt-tttcaataaa------ctt 3414

GH1-ctctgcagcacatgatcttgcttctattaatatccttcaaatcaacattttt--acaagttcctagcccaacattcctatgatgtctctcggac 4212
    |||||||  | |||||||||||||||||  |||| |||||||||||||||||    ||| ||||||| |||||||| || ||| |||| ||||
GH2-ctctgcagtatatgatcttgctactattgctatcttcaaatcaacattttttttacaagtttctagcccaacattcctattgtgtcccttggac 3514

GH1-aatttagggcctggattcaatcctgtatccgtatcgcagacgctccattgaaatgtaaaggcaatgttcctgcgttcgcgggagactgcattc 4297
    |||||||| |  |||||| |||| |||||||||||  ||||||| ||||| |||||    ||||||
GH2-aacttaaggc-tggatttaattcttatcgcagatgctccattgaaatgtcaaggcagttcc----------ctgcgttc 3584
```

TABLE 2

Growth performance and serum GH levels of transgenic and control coho salmon. Fish were sampled at 12 months post-fertilization.

| | Number in group | Weight (g) | Length (cm) | Condition Factor' | Weight SGR | Length SGR | Serum GH (ng/mL) |
|---|---|---|---|---|---|---|---|
| Uninjected Controls | 792 | 13.53 ± 0.13 | 10.41 ± 0.03 | 1.16 ± 0.0003 | 1.23 ± 0.003 | 0.388 ± 0.0009 | ND |
| Transgenic (microinjected) | 74 | 158.46 ± 13.69 | 21.56 ± 0.82 | 1.24 ± 0.016 | 1.89 ± 0.04 | 0.601 ± 0.014 | 11.02 ± 3.53 (10) |
| Non-transgenic (microinjected) | 999 | 18.58 ± 0.75 | 11.34 ± 0.06 | 1.115 ± 0.006 | 1.30 ± 0.004 | 0.413 ± 0.001 | 0.26* ± 0.03 (9) |

ND-Not Determined.
SGR-Specific Growth Rate (% body weight (W) or Length (L) per day) = $\Delta$ln (W or L)/$\Delta$t (days) × 100.
'Condition factors = $W/L^3$ × 100.
*The levels of GH in 5 out of 9 individuals in this group were at the minimum detection limit of the Radio-immune assay used (0.2. ng/mL).

I claim:

1. A promoter sequence, for use in preparing a gene construct for incorporation into the genome of fish and causing enhanced expression of growth hormone transgene, comprising a nucleotide sequence including the sockeye (*O. nerka*) metallothionein MT-Type B gene promoter having the 318 base pair sequence in SEQ.ID. No.2.

2. A vector or gene construct for preparing transgenic fish comprising:

(i) a promoter sequence comprising a metallothionein MT-B gene promoter from the sockeye species of the family Salmonidae; operably linked to
(ii) a GH gene from the same species as in (i) and operably linked to
(iii) a GH gene terminator from the same species as in (i), said promoter causing enhanced expression of the GH gene.

3. A salmonid fish cell stably transformed with the construct of claim 2, the construct being within the genome and the cell having enhanced GH gene expression compared to a non-transformed salmonid fish cell.

4. A salmonid transgenic fish incorporating transformed cells of claim 3, said fish having the construct within its genome and elevated plasma growth hormone level and increased growth rate compared to non-transgenic salmonid fish.

5. The transgenic fish of claim 4 wherein the GH gene to be expressed codes for sockeye salmon growth hormone GH Type 1 or Type 2.

6. A method of inducing at least one of accelerated growth, and early smoltification in salmonid fish comprising a) insertion of the DNA construct of claim 2 into the genome of the fish and wherein the inserted DNA construct comprises the full length growth hormone Type 1 gene including all naturally-occurring introns; and b) expression of the GH gene.

7. In the process of preparing transgenic salmonid fish having accelerated growth by transforming a fish cell with an expression vector, the improvement comprising combining in the vector sockeye salmonid metallothionein MT-B gene promoter DNA sequence, and sockeye salmonid GH gene DNA sequence and providing for expression.

8. A growth hormone gene for sockeye salmon (*O. nerka*) comprising at least one GH gene sequence selected from GH1 (bases 1–4138 in SEQ ID No. 3) and GH2 (bases 1–3440 in SEQ ID No. 4) in Table 1.

\* \* \* \* \*